United States Patent [19]

Shoesmith, deceased

[11] Patent Number: Plant 5,816

[45] Date of Patent: Dec. 2, 1986

[54] CHRYSANTHEMUM PLANT NAMED HOPSCOTCH

[75] Inventor: Leonard H. Shoesmith, deceased, late of Woking Surrey, England, by May Victoria Shoesmith, executrix

[73] Assignee: Ball Pan Am Plant Company, Parrish, Fla.

[21] Appl. No.: 681,422

[22] Filed: Dec. 13, 1984

[51] Int. Cl.[4] ..... A01H 5/00

[52] U.S. Cl. ..... Plt./74

[58] Field of Search ..... Plt./74

*Primary Examiner*—R. E. Bagwill

*Attorney, Agent, or Firm*—Schwartz, Jeffery, Schwaab, Mack, Blumenthal & Evans

[57] ABSTRACT

A new and distinct cultivar of Chrysanthemum named Hopscotch having flat capitulum form and single capitulum type, yellow ray floret color, excellent flower substance, diameter of capitulum 9.5 to 11.5 cm., medium pot plant height and semi-upright branching pattern.

1 Drawing Figure

The present invention comprises a new and distinct cultivar of *Chrysanthemum morifolium,* Ramat., named Hopscotch.

Hopscotch is a product of a planned breeding program which had the objective of creating new Chrysanthemum cultivars with large capitulum type, yellow ray floret color, good flower substance, nine week flower response, and having the ability to produce commercially acceptable quality year round. Such traits in combination were not present or needed improvement in previously available commercial cultivars.

Hopscotch was originated from a hybridization made in a controlled breeding program in Westfield, Woking, England in 1978. The male and femals parents are unknown at this time.

Hopscotch was discovered and selected as one flowering plant within the progeny of the stated cross by Leonard H. Shoesmith in November 1979 in a controlled environment in West Chicago, Ill. and given the code name P9-1288-4.

The first act of asexual reproduction of Hopscotch was accomplished when vegatative cuttings were taken from the initial selection in February 1980 in a controlled environment in West Chicago, Ill. by a technician working under formulations established and supervised by Leonard H. Shoesmith. Horticultural examination of selected units initiated in March 1980 has demonstrated that the combination of characteristics as herein disclosed for Hopscotch are firmly fixed and are retained through successive generations of asexual reproduction.

Hopscotch has not been observed under all possible environmental conditions. The phenotype may vary significantly with variations in environment such as temperature, light intensity and day length. The observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Hopscotch which in combination distinguish this Chrysanthemum as a new and distinct cultivar:

(1) Flat capitulum form.

(2) Single capitulum type.

(3) Yellow ray floret color.

(4) Excellent flower substance.

(5) Diameter across face of capitulum ranging from 9.5 to 11.5 cm. at maturity.

(6) Medium pot plant height of about 300 mm from edge of pot. Applications of B-9 may be used to control plant height.

(7) Semi-upright branching pattern.

(8) Flower color varies somewhat depending on growing conditions.

Of the many commercial cultivars known to the present inventor, the most similar in comparison to Hopscotch is the Cymbals, disclosed in U.S. Plant Pat. No. 5,019, granted Mar. 29, 1983. In comparison to Cymbals, Hopscotch has 5 to 7 days earlier response; is more vigorous; has 1 to 2 more rows of ray florets; is lighter in color; is less sensitive to high temperatures, and its leaves do not fleck under high temperatures. The flower form of Hopscotch is similar to the same characteristic of Cymbals.

The accompanying photographic drawing depicts typical inflorescense and foliage characteristics of Hopscotch, with colors being as nearly true as possible with illustrations of this type.

In the following description, color references are made to The Royal Horticultural Society Colour Chart. The color values were determined at approximately 11:00 a.m. on Sept. 14, 1983, under 800 foot-candles of light intensity at Parrish, Fla.

Classification:

*Botanical.—Chrysanthemum morifolium,* Ramat., cv Hopscotch.

*Commercial.*—Disbud daisy pot.

I. INFLORESCENCE

A. Capitulum:

*Form.*—Flat.

*Type.*—Daisy.

*Diameter Across Face.*—9.5 to 11.5 cm.

B. Corolla of ray florets:

*Color (general tonality from a distance of three meters).*—Darker yellow in winter to a lighter yellow in summer.

*Color (lower surface).*—5C.

*Color (upper surface).*—5A.

C. Corolla of disc florets:

*Color* (*mature*).—Yellow.

*Color* (*immature*).—Greenish yellow.

D. Reproductive organs:

*Androecium.*—Present in disc florets only — abundant.

*Gynoecium.*—Present in both ray and disc florets — abundant.

II. PLANT

A. General appearance:

*Height.*—Upright, approximately 300 mm at flowering with application of B-9.

B. Foliage:

*Color* (*lower surface*).—137B.

*Color* (*upper surface*).—137A.

*Shape.*—Deeply lobed and somewhat serrated.

It is claimed:

1. A new and distinct cultivar of *Chrysanthemum morifolium,* Ramat., plant named Hopscotch, as described and illustrated, having flat capitulum form and single capitulum type, yellow ray floret color, excellent flower substance, diameter of capitulum 9.5 to 11.5 cm., medium pot plant height and semi-upright branching pattern.

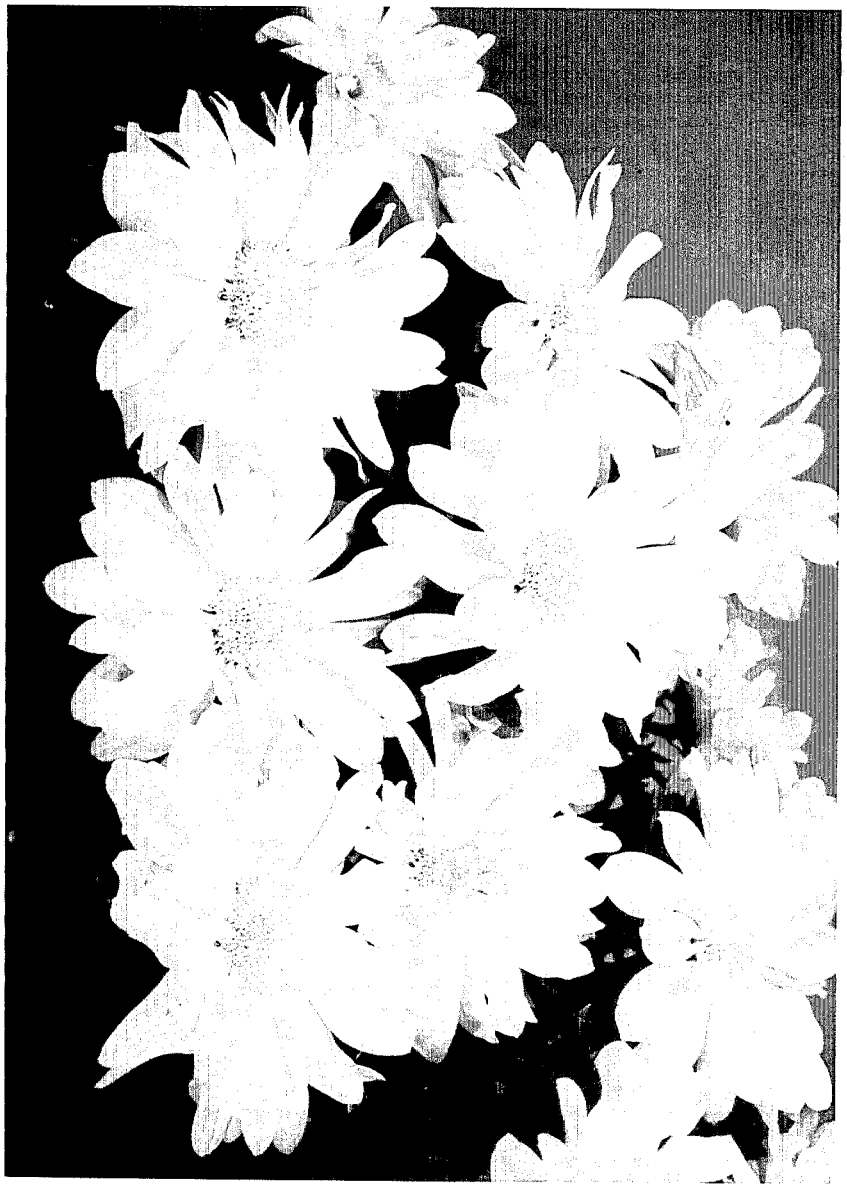

* * * * *